United States Patent [19]

Kratoska et al.

[11] Patent Number: 5,328,465
[45] Date of Patent: Jul. 12, 1994

[54] APPARATUS AND METHOD FOR LIMITING ACCESS TO SEPTUM

[75] Inventors: Paul S. Kratoska, Brooklyn Park; Larry D. Kuecker, Coon Rapids; Douglas O. Hankner, New Brighton, all of Minn.

[73] Assignee: Medtronic, Inc., Minneapolis, Minn.

[21] Appl. No.: 969,599

[22] Filed: Oct. 30, 1992

[51] Int. Cl.⁵ .............................................. A61M 5/00
[52] U.S. Cl. ..................................... 604/93; 604/175; 128/DIG. 12
[58] Field of Search .............. 604/93, 115–117, 604/122, 175, 131–133, 140–141, 149, 151, 256; 128/DIG. 12

[56] References Cited

U.S. PATENT DOCUMENTS

| | | | |
|---|---|---|---|
| 4,286,584 | 11/1981 | Sampson | 128/1 |
| 4,496,343 | 1/1985 | Prosi et al. | 604/86 |
| 4,687,468 | 8/1987 | Gianturco | 604/153 |
| 4,710,174 | 12/1987 | Moden et al. | 604/175 |
| 4,760,837 | 8/1988 | Petit | 128/1 |
| 4,781,680 | 11/1988 | Redmond et al. | 604/93 |
| 4,857,053 | 8/1989 | Dalton | 604/93 |
| 4,904,241 | 2/1990 | Bark | 604/93 |
| 5,006,115 | 4/1991 | McDonald | 604/175 |
| 5,009,644 | 4/1991 | McDonald | 604/175 |
| 5,061,242 | 10/1991 | Sampson | 604/118 |

Primary Examiner—C. Fred Rosenbaum
Assistant Examiner—Corrine Maglione
Attorney, Agent, or Firm—Harold R. Patton; Terry L. Wiles

[57] ABSTRACT

An apparatus and method for limiting access to a septum in a body implanted device. The apparatus includes a screen member which covers the septum. The screen member has a plurality of openings which are sized such that needles larger than a predetermined size will not pass through the openings. Needles of a size less than the predetermined size of the openings will pass through and be provided access to the septum.

12 Claims, 3 Drawing Sheets

APPARATUS AND METHOD FOR LIMITING ACCESS TO SEPTUM

FIELD OF THE INVENTION

This invention relates generally to apparatus and methods for limiting access to body implanted septums. More particularly, the invention is directed to an improved apparatus with a screen member which covers the septum and which has a plurality of openings sized to limit the access to the septum to needles which will fit within the openings.

BACKGROUND OF THE INVENTION

Implantable devices such as drug pumps are in frequent use for delivering drugs or other liquid medications over long periods of time to selected locations in the human body. These devices commonly include a drug reservoir, catheter means connected to the reservoir to transport the drug and a pumping mechanism to propel the drug in some metered or constant flow dosage to the desired location. Over time, the drug in the reservoir becomes depleted and it is necessary to refill the device with a new supply of drug. In order to avoid the need for surgery in order to access and refill the device, it is desirable to have the ability to refill the drug reservoir percutaneously. This is commonly done by providing the drug pump with a resilient resealable reservoir fill port septum which is accessible by injecting a hypodermic needle through the skin and into the septum thereby providing access to refill the reservoir.

In such devices a catheter access port septum may be provided in addition to the reservoir fill port septum. The catheter access port septum is also accessible percutaneously by hypodermic needle. This septum provides direct access to the catheter bypassing the pump and allows a bolus of drug or fluid medication to be administered directly into the body at the site of the catheter.

Although providing a catheter access port septum is both desirable and advantageous a problem can develop if the person refilling the reservoir incorrectly injects the drug into the catheter access port septum instead of the reservoir fill port septum. This results in the drug being administered directly to the body. This may potentially cause an overdose of drug or other serious problems since the drug is meant to be administered by the pump over a period of time.

In the field of implantable drug pumps various devices have been used to enable the reservoir fill port septum to be correctly located. For example, in U.S. Pat. No. 4,286,584 to Sampson et al., an apparatus is disclosed which, when manipulated over the body at the site of the implanted device, produces an energy pattern which designates the location of the septum. In the SynchroMed(TM) Infusion System marketed by Medtronic, Inc., the assignee of the present invention, a template is used which is placed over the site of the implanted device to located the septum.

Although these devices are useful in locating the reservoir fill port they do not prevent the occurrence of human error which could result in the drug being injected into the wrong septum. None of the current devices are equipped with any safety feature which would prevent the inadvertent delivery of drug meant for the reservoir into the catheter access port septum. Present devices rely primarily on the physical separation of the septums in order to prevent possible misdelivery of drug.

Therefore, even though there are devices, as mentioned above, which will accurately locate the reservoir fill port if used correctly, the possibility of human error still exists. This error can result in the inadvertent injection of the drug meant for the reservoir directly into the catheter access port septum and into the body. Thus, a need exists for a device or method which would eliminate or at least reduce the possibility of inadvertent injections of drug directly into the catheter access port.

SUMMARY OF THE INVENTION

In accordance with the present invention, an apparatus for limiting percutaneous access by needle to a septum in a device implanted in a body is provided. The apparatus has a screen member covering the septum, the screen member having a plurality of openings. The openings are of a predetermined size, such that needles larger than the predetermined size will not pass through the screen member and penetrate the septum. In a one embodiment the openings are generally circular. The apparatus further includes means for fixing the screen member in a position covering the septum.

The means for fixing the screen member in position may comprise continuous side walls interconnected with the implanted device and with the septum, the continuous side walls being connected to the screen member to support the screen member in a position covering the septum.

In one embodiment the screen member includes an outer surface and an inner surface. The openings are shaped such that they taper inwardly from the outer surface to the inner surface, such that the openings are larger at the outer surface than at the inner surface.

The predetermined size of the openings is a matter of design choice. In one embodiment the predetermined size is large enough to allow a 25 gauge needle to penetrate the septum but small enough so that a 22 gauge needle will not pass through the screen member to penetrate the septum.

In another aspect, the invention is used with an implantable drug pump having a reservoir for containing a drug, a reservoir fill port septum, catheter means for connecting the reservoir with the location within the body where the drug is to be administered, and a catheter access port septum for direct access to the catheter means. In this aspect, the invention is an apparatus for limiting access to the catheter access port septum. The apparatus includes a screen member covering the catheter access port septum. The screen member has a plurality of openings, the openings being of a predetermined size, such that needles larger than the predetermined size will not pass through the screen member and penetrate the septum. The apparatus further includes means for fixing the screen member in position covering the catheter access port septum.

In this embodiment the means for fixing the screen member in position may comprise continuous side walls interconnected with the implantable drug pump and with the catheter access port septum, the continuous side walls being connected to the screen member to support the screen member in a position covering the catheter access port septum. Further, the shape of the predetermined openings may be generally circular.

In this embodiment the screen member may include an outer surface and an inner surface. The openings are shaped such that they taper inwardly from the outer surface to the inner surface, such that the openings are larger at the outer surface than at the inner surface.

In another aspect, the invention is a method used in connection with an implantable drug pump having a reservoir for containing the drug, a reservoir fill port septum, catheter means for connecting the reservoir with the location within the body where the drug is to be administered, and a catheter access port septum for direct access to the catheter means. In this aspect the invention is a method for limiting access to the catheter access port septum. The method comprises covering the catheter access port septum with a screen member. The screen member has a plurality of openings of a predetermined size, such that needles larger than the predetermined size will not pass through the screen member and penetrate the septum. The method further comprises connecting the screen member to the implantable drug pump in a location such that the catheter access port septum is covered.

BRIEF DESCRIPTION OF THE DRAWINGS

The foregoing and other aspects of the present invention will be best appreciated with reference to the detailed description of the invention, which follows, when read in conjunction with the accompanying drawings wherein.

DETAILED DESCRIPTION OF THE INVENTION

Figure 1:
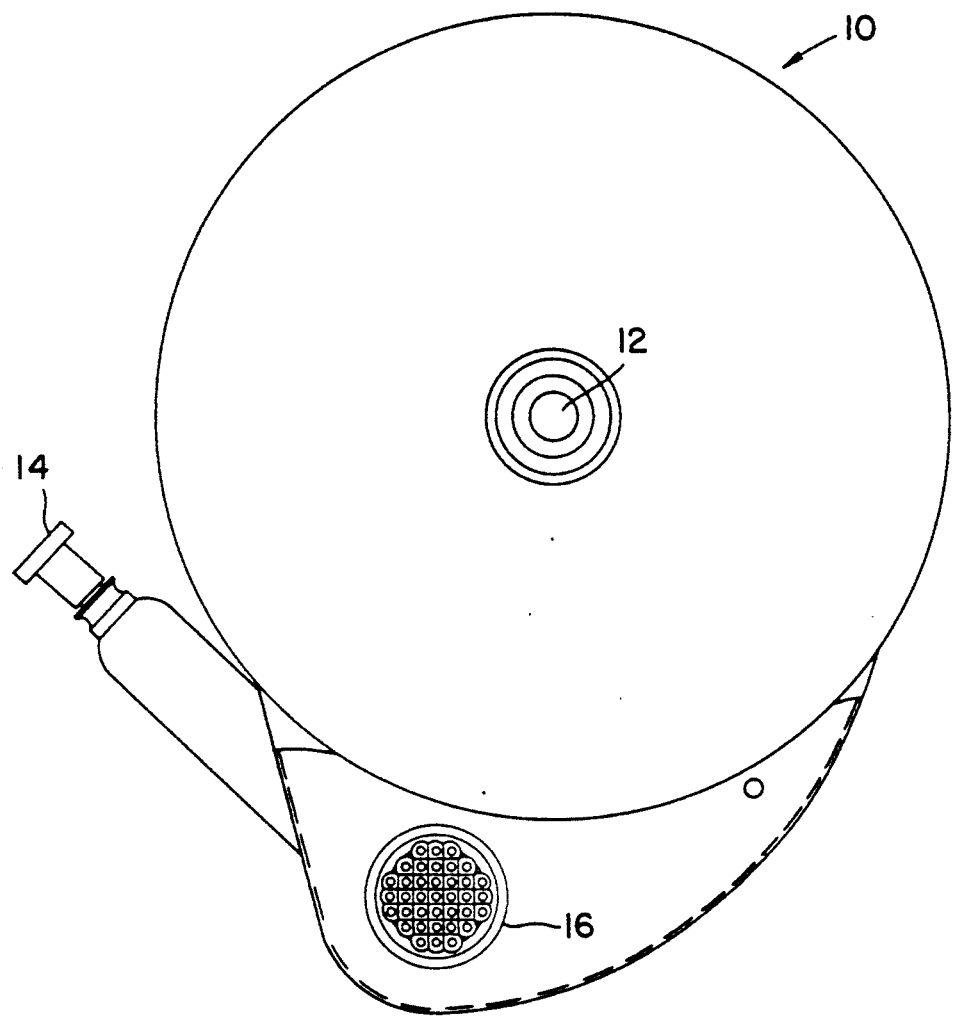
FIG. 1 is a top view of an implantable drug pump incorporating the present invention.
Figure 2:
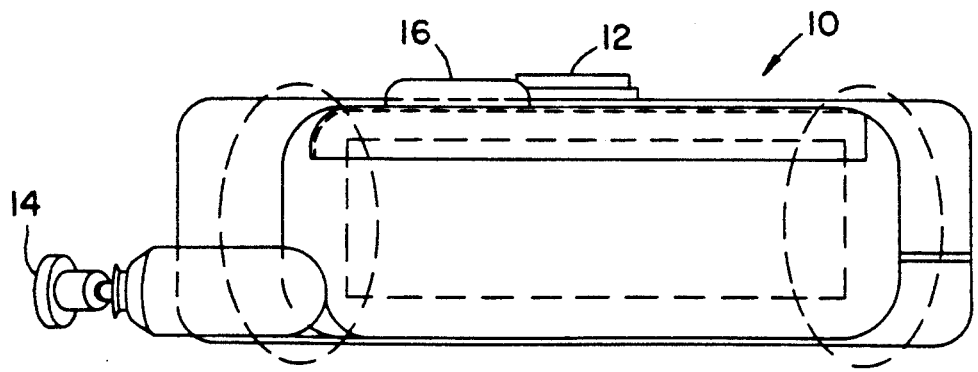
FIG. 2 is a side view of the drug pump of FIG. 1.

With reference to FIGS. 1 and 2 there is shown top and side views, respectively, of a body implantable drug pump 10 incorporating the present invention. Pump 10 includes a reservoir fill port septum 12 which is percutaneously accessible by a hypodermic needle. Fill port septum 12 is comprised of a resilient, resealable material such as silicone rubber which is durable enough to withstand numerous punctures without leaking. A reservoir (not shown) may be filled by inserting a needle through the skin into fill port septum 12 and injecting the drug into the reservoir. Pump 10 includes pumping means (not shown) for delivering constant or metered doses of the drug out of a catheter outlet port 14. Catheter outlet port 14 is connected to a catheter (not shown) which is positioned so that the drug is pumped out of outlet port 14 through the catheter to a selected location with the body. Drug pump 10 is of conventional design known in the art such as the SynchroMed(TM) Infusion System manufactured by Medtronic, Inc. of Minneapolis, Minn.

Drug pump 10 further includes a catheter access port 16. Access port 16 is shown in more detail in FIGS. 4, 5 and 6 which will be discussed in detail hereafter. Catheter access port 16 provides direct percutaneous access by hypodermic needle to catheter outlet port 14. This allows the direct injection through access port 16 of a bolus of medication or drug to the site of the catheter without going through the pump 10.

Figure 4:
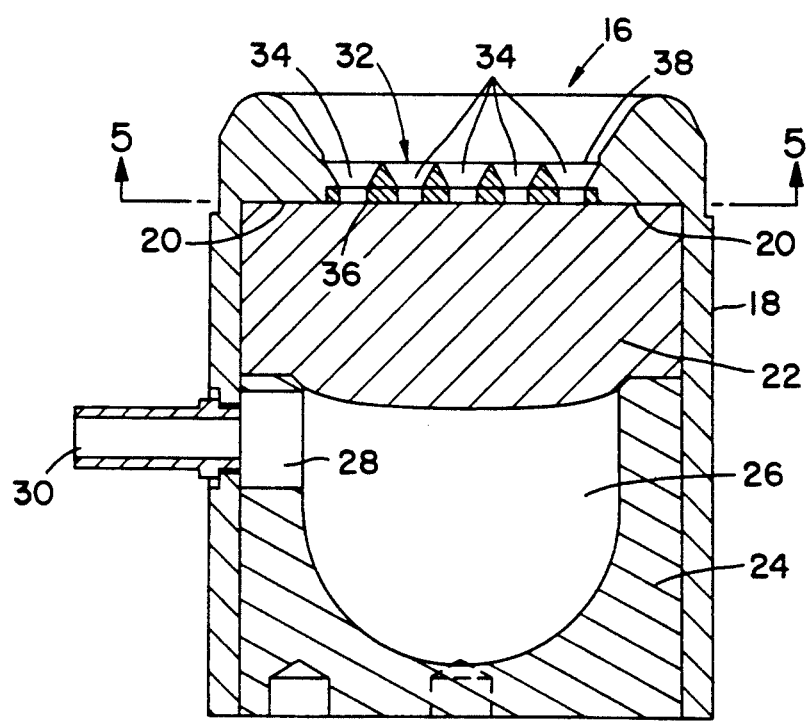
FIG. 4 is a catheter access port septum according to the present invention.

With reference to FIG. 4 there is illustrated a sectional view of catheter access port 16. Access port 16 includes continuous side walls 18 which have an overhanging edge 20. A resealable septum 22 lies within side walls 18. Septum 22 is held against overhanging edge 20 by a rigid plug 24. Plug 24 is U-shaped to define a central space 26 lying between plug 24 and septum 22. Plug 24 includes an opening 28 which provides a fluid path between space 26 and an outlet 30. Outlet 30 provides a direct fluid path to catheter outlet port 14 so that any fluid medication injected through septum 22 into central space 26 will flow directly to the catheter.

With continued reference to FIG. 4 it can be seen that septum 22 is covered on its exterior side opposite space 26 by a screen member 32. Screen member 32 can be constructed as an integral portion of side walls 18, as shown, or could be made of a separate component which is then rigidly affixed to continuous side walls 18. Alternatively, screen member 32 could be of separate construction and sized so that its edges would fit within the area defined by side walls 18 and under overhanging edge 20. Screen member 32 could thus be held in place in the same manner as septum 22, being held between septum 22 and overhanging edge 20. The particular manner in which screen member 32 is held in place is thus a matter of design choice, it being necessary only that there be some means for fixing the position of screen member 32 so that it covers septum 22.

Figure 3:
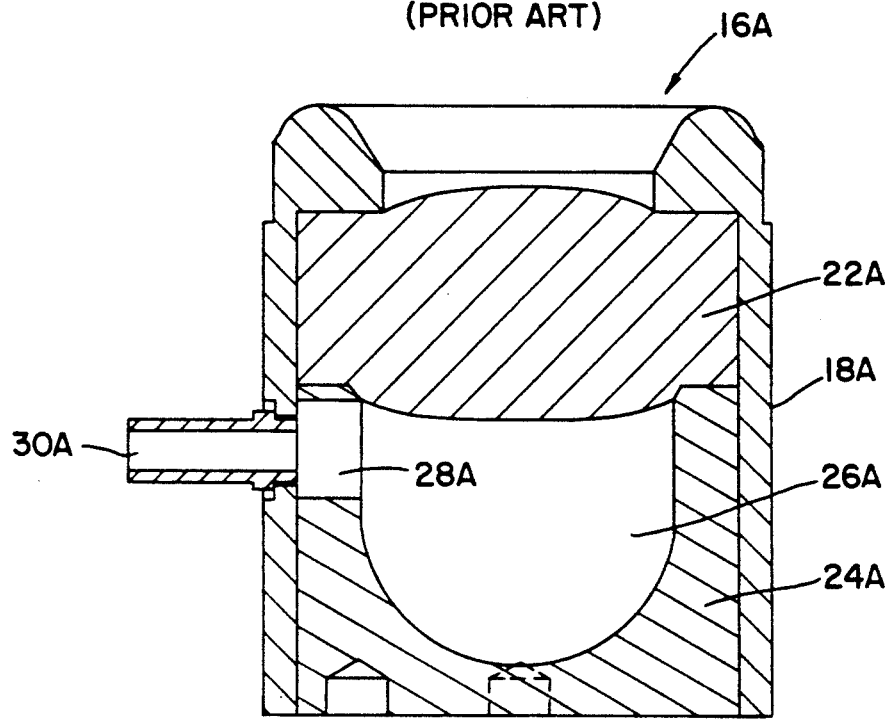
FIG. 3 is a sectional view of a catheter access port septum according to the prior art.

In FIG. 3 a prior art catheter access port is illustrated. In FIG. 3 like elements are given like reference numerals with the addition of an "A". This drawing figure illustrates that each of the elements of the prior art are contained in the present invention with the exception of screen member 32 and the means in which screen member 32 is connected to the catheter access port over the septum.

Figure 5:
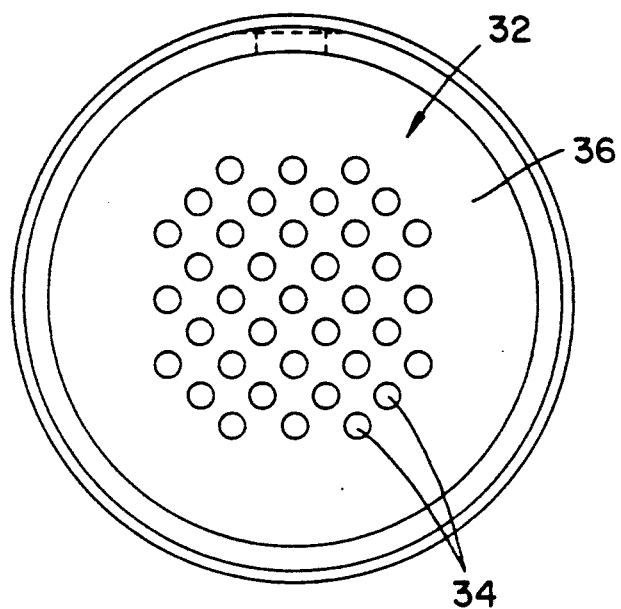
FIG. 5 is a sectional view of the screen member taken along line 5—5 in FIG. 4.
Figure 6:
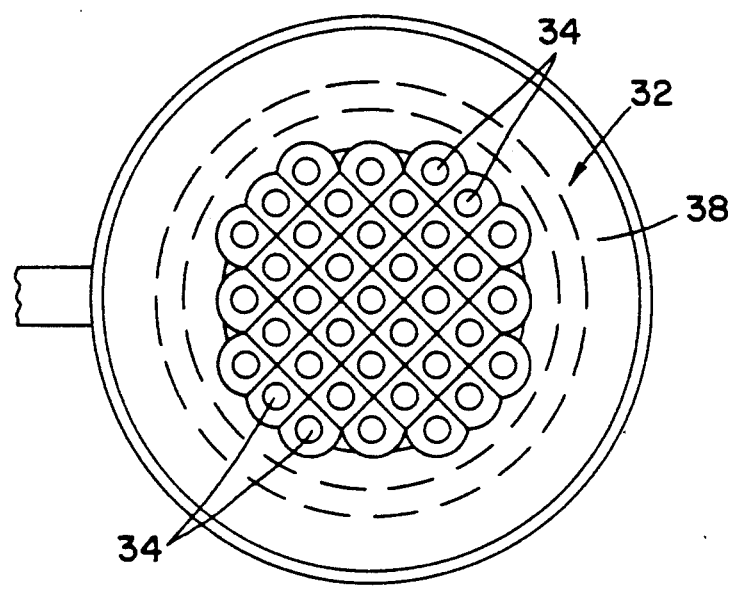
FIG. 6 is a top view of the catheter access port septum of FIG. 4.

The particular construction of screen member 32 can be explained with reference to FIGS. 5 and 6. FIG. 5 is a sectional view of the inner surface 36 of screen member 32. FIG. 6 is a top view of catheter access port 16 showing the outer surface 38 of screen member 32. Screen member 32 is preferably of one piece construction and may be comprised of a durable material such as titanium into which is drilled or machined a plurality of openings 34. Openings 34 may be of any desired shape but are preferably circular.

In the embodiment illustrated in FIGS. 4, 5 and 6 openings 34 taper inwardly from outer surface 38 to a position just above inner surface 36 to create a funnel shaped hold through screen member 32. Alternatively, the taper could extend all the way to inner surface 36 to form a cone shaped hold. Thus, openings 34 are of larger size or diameter at the outer surface than at the inner surface. Additionally, as apparent in FIG. 6, it is preferable that the openings 34 form a continuous pattern across outer surface 38 so that any needle which is to be inserted is guided through screen member 32 and out an opening 34 at the inner surface 36.

The openings 34 in screen member 32 are sized to prohibit access to catheter access port septum 22 of a needle in excess of a certain size or gauge. For example, the model 8551 refill kit used to refill the SynchroMed(TM) drug pump includes a 22 gauge needle. Thus, in order to prevent the inadvertent insertion of the refill needle into the catheter access port septum, the openings 34 are sized so that a 22 gauge needle will not pass through the screen. Therefore, the septum can not be punctured and the possibility of inadvertent injection directly into the body through the catheter access port septum is virtually eliminated. Should direct injection of a bolus of medication or drug through the catheter access port septum be desired a smaller needle, for example a 25 gauge needle is used. The screen member is sized so that access is permitted to the 25 gauge needle but prohibited to the 22 gauge needle.

From the forgoing detailed description of specific embodiments of the invention, it should be apparent that an apparatus and method for limiting access to a septum has been disclosed. Although a particular embodiment of the invention has been disclosed herein in detail, this has been done for the purpose of illustration only, and is not intended to be limiting with respect to the scope of the appended claims, which follow. In particular, it is contemplated by the inventors that various substitutions, alterations and modifications may be made to the embodiments of the invention described herein without departing from the spirit and scope of the invention as defined by the claims. For instance, the choice of materials or variations of the shape of the openings in the screen member are believed to be a matter of routine for a person of ordinary skill in the art with knowledge of the embodiments disclosed herein. Likewise, although the embodiments disclosed relate primarily to implantable drug pumps, the present invention could be used for other applications where it is desirable to limit access to a septum.

We claim:

1. Apparatus for limiting percutaneous access by needle to a septum in a device implanted in a body, comprising:
    a screen member covering the septum, the screen member having a plurality of openings, said openings being of a predetermined size, and screen member further having an outlet surface and an inner surface and wherein said openings taper inwardly from said outer surface to said inner surface, such that said openings are larger at said outer surface than at said inner surface and that needles larger than said predetermined size will not pass through said screen member and penetrate the septum, and
    means for fixing said screen member in position covering the septum.

2. In an implantable drug pump having a reservoir for containing the drug, a reservoir fill port septum, catheter means for connecting the reservoir with the location within the body where the drug is to be administered, and a catheter access port septum for direct access to the catheter means, an apparatus for limiting access to the catheter access port septum comprising:
    a screen member covering the catheter access port septum, the screen member having a plurality of openings, said openings being a predetermined size, said screen member further having an outer surface and an inner surface and wherein said openings taper inwardly from said outer surface to said inner surface, such that said openings are larger at said outer surface than at said inner surface and that needles larger than said predetermined size will not pass through said screen member and penetrate the septum, and
    means for fixing said screen member in position covering the catheter access port septum.

3. An implantable drug pump having a drug storage reservoir and means to pump the drug through a catheter to a desired location in the body, the drug pump comprising:
    a reservoir fill port septum for providing percutaneous access to the reservoir;
    an outlet port connected to the reservoir;
    a catheter access port in fluid communication with said outlet port;
    a catheter access port septum affixed to said catheter access port for providing percutaneous access to said catheter access port, and
    a screen member covering said catheter access port septum, the screen member having a plurality of openings, said openings being of a predetermined size, such that needles larger than said predetermined size will not pass through said screen member and penetrate the catheter access port septum.

4. The implantable drug pump of claim 3 wherein said openings are generally circular.

5. The apparatus of claim 3 wherein said screen member includes an outer surface and an inner surface and wherein said openings taper inwardly from said outer surface to said inner surface, such that said openings are larger at said outer surface than at said inner surface.

6. In an implantable drug pump having a reservoir for containing the drug, a reservoir fill port septum, catheter means for connecting the reservoir with the location within the body where the drug is to be administered, and a catheter access port septum for direct access to the catheter means, a method for preventing penetration of the catheter access port septum when the drug reservoir is refilled comprising:
    covering the catheter access port septum with a screen member, the screen member having a plurality of openings, said openings being of a predetermined size, such that needles larger than said predetermined size will not pass through said screen member and penetrate the catheter access port septum, and
    providing a refill kit for use when the reservoir is refilled, said refill kit including a hypodermic needle larger than said predetermined size.

7. The method of claim 6 wherein said openings are generally circular.

8. The method of claim 6 wherein the predetermined size of said openings is large enough to allow a 25 gauge needle to penetrate the catheter access port septum but small enough so that a 22 gauge needle will not pass through said screen member to penetrate the catheter access port septum.

9. In an implantable drug pump having a reservoir for containing the drug, a reservoir fill port septum, catheter means for connecting the reservoir with the location within the body where the drug is to be administered, and a catheter access port septum for direct access to the catheter means, a method for limiting access to the catheter access port septum comprising:
    covering the catheter access port septum with a screen member, the screen member having a plurality of openings, said openings being of a predetermined size, said screen member further having an outer surface and an inner surface and wherein said openings taper inwardly from said outer surface to said inner surface, such that said openings are larger at said outer surface than at said inner surface and that needles larger than said predetermined size will not pass through said screen member and penetrate the septum, and connecting said screen member to the implantable drug pump in a location such that the catheter access port septum is covered.

10. A method of filling a drug reservoir in an implanted drug pump, the drug pump having a reservoir fill port septum, an outlet port for connection to a catheter, a catheter access port and a catheter access port septum, the method comprising:

covering the catheter access port septum with a screen member, the screen member having a plurality of openings, said openings being of a predetermined size, such that needles larger than said predetermined size will not pass through said screen member and penetrate the catheter access port septum, and selecting a hypodermic needle larger than said predetermined size, and filing said hypodermic needle with a desired quantity and type of fluid medication, and percutaneously inserting said hypodermic needle through the reservoir fill port septum into the reservoir and injecting the drug into the reservoir.

11. The method of claim 10 wherein said openings are generally circular.

12. The method of claim 10 wherein said screen member includes an outer surface and an inner surface wherein said openings taper inwardly from said outer surface to said inner surface, such that said openings are larger at said outer surface than at inner surface.

* * * * *